United States Patent

Adamczyk et al.

Patent Number: 5,691,456
Date of Patent: Nov. 25, 1997

[54] REAGENTS AND METHODS FOR THE DETECTION AND QUANTIFICATION OF THYROXINE IN FLUID SAMPLES

[75] Inventors: Maciej Adamczyk, Gurnee; Donald D. Johnson, Lindenhurst; Phillip G. Mattingly, Grayslake; Diana E. Clarisse, Naperville; Joan D. Tyner, Beach Park; Mary M. Perkowitz, Lake Zurich, all of Ill.

[73] Assignee: Abbott Laboratories, Abbott Park, Ill.

[21] Appl. No.: 444,128

[22] Filed: May 18, 1995

Related U.S. Application Data

[60] Division of Ser. No. 275,064, Jul. 13, 1994, Pat. No. 5,593,896, which is a continuation-in-part of Ser. No. 859,775, Mar. 30, 1992, Pat. No. 5,352,803.

[51] Int. Cl.⁶ .................................................. C07K 17/00
[52] U.S. Cl. .................................... 530/405; 530/807
[58] Field of Search ......................... 435/188; 530/807, 530/405

[56] References Cited

U.S. PATENT DOCUMENTS

| | | | |
|---|---|---|---|
| 4,341,865 | 7/1982 | Voss | 435/188 |
| 4,430,263 | 2/1984 | March et al. | 436/500 |
| 4,888,296 | 12/1989 | Siebert et al. | 436/500 |

OTHER PUBLICATIONS

M. Bhattacharya et al., Indian Journal of Experimental Biology, vol. 26, pp. 990–992 1988.

*Primary Examiner*—Mary E. Ceperley
*Attorney, Agent, or Firm*—Lawrence S. Pope

[57] ABSTRACT

Immunoassay methods and reagents for the specific quantification of thyroxine in a test sample are disclosed employing antibodies prepared with thyroxine derivatives of the formula:

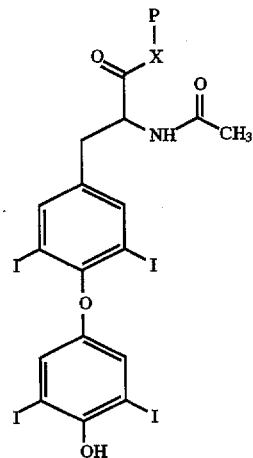

wherein P is an immunogenic carrier material and X is a linking moiety.

The present invention also describes the synthesis of unique labelled reagent of the formula:

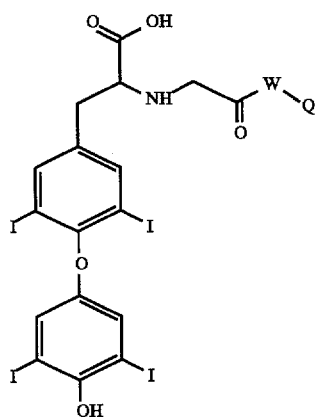

wherein Q is a detectable moiety and W is a linking moiety, preferably fluorescein or a fluorescein derivative.

1 Claim, 2 Drawing Sheets

FIG. 1   SYNTHESIS OF THE L-THYROXINE IMMUNOGEN
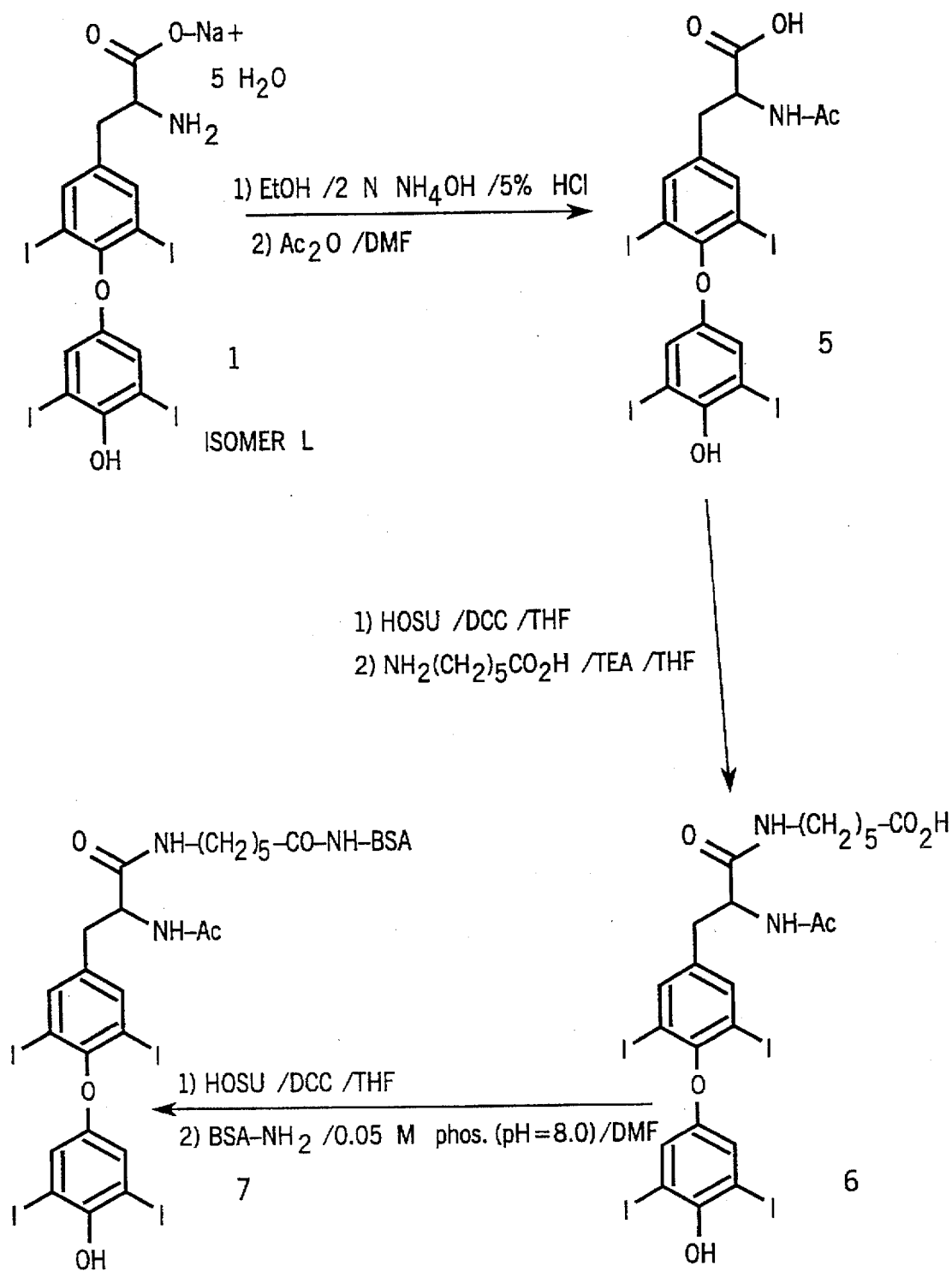

FIG. 2  SYNTHESIS OF THE L-THYROXINE TRACER
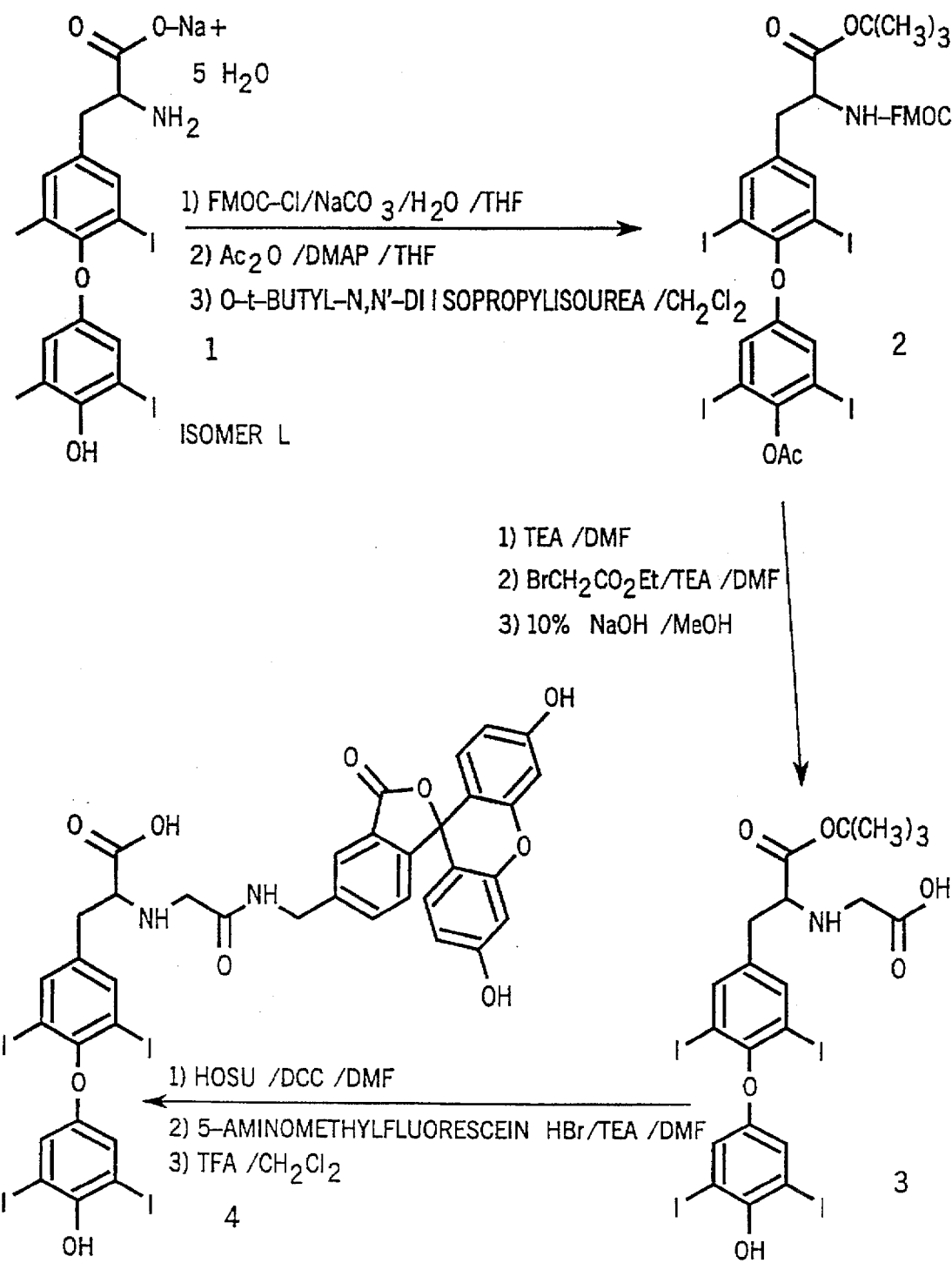

REAGENTS AND METHODS FOR THE DETECTION AND QUANTIFICATION OF THYROXINE IN FLUID SAMPLES

This application is a division of U.S. patent application Ser. No. 08/275,064, filed Jul. 13, 1994, now U.S. Pat. No. 5,593,896, which is a continuation-in-part application of U.S. patent application Ser. No. 859,775 of P. G. Mattingly, filed Mar. 30, 1992, now U.S. Pat. No. 5,352,803, entitled "5(6)-Methyl Substituted Fluorescein Derivatives".

FIELD OF THE INVENTION

The present invention relates to the immunoassay quantification of thyroxine in a test sample. In particular, the present invention relates to immunogens, antibodies prepared from such immunogens, and labelled reagents for the specific quantification of thyroxine in a test sample, preferably for use in fluorescence polarization immunoassays.

BACKGROUND OF THE INVENTION

The amino acid 3,5,3',5'-tetraiodo-L-thyronine, commonly called thyroxine and often referred to as $T_4$, is the predominant iodothyronine secreted from the thyroid gland. $T_4$ is responsible for regulating diverse biochemical processes throughout the body, which are essential for normal metabolic and neural activities. The measurement of serum $T_4$ concentration has become the common initial test in the diagnosis of altered thyroid function. Several conditions other than thyroid disease may cause abnormal serum levels of $T_4$. Among these are pregnancy, estrogenic or androgenic steroids, oral contraceptives, hydantoins and salicylates, stress, hyper- and hypoproteinemia, and conditions (hereditary or acquired) which cause alterations in serum levels of thyroid binding globulin (TBG), the major serum $T_4$ transport system.

The concentration of thyroxine in the bloodstream is extremely low and can only be detected with very sensitive techniques. Approximately 0.05% of the total circulating thyroxine is physiologically active (i.e. free thyroxine). The remaining circulating thyroxine is bound to proteins, primarily thyroxine binding globulin (TBG). Thyroxine will also bind to other binding proteins, particularly, thyroxine binding pre-albumin and albumin. Early $T_4$ determinations were indirect measurements of the concentration of protein-bound or butanol-extractable iodine in serum. Later, competitive protein binding (CPB) assays were developed. More recently, radioimmunoassay procedures have been developed which use both polyclonal and monoclonal antibodies, such as disclosed in U.S. Pat. Nos. 4,636,478 and 4,888,296 to Siebert et al., which disclose radioimmunoassay for thyroxine using specific monoclonal antibodies recognizing L-thyroxine. In general, radioimmunoassay procedures in the art measure counts of radioactivity which are related to the binding of the antibody to L-thyroxine.

D-thyroxine is a non-naturally occurring isomer of thyroxine. Both L- and D-thyroxine are represented by Formula 1 below:

FORMULA 1
L- AND D- THYROXINE

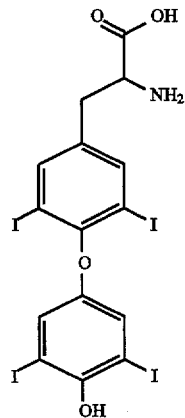

More recently, fluorescent polarization techniques have been used to assay for thyroxine. Fluorescent polarization techniques are based on the principle that a fluorescent labelled compound when excited by linearly polarized light will emit fluorescence having a degree of polarization inversely related to its rate of rotation. Therefore, when a fluorescent labelled tracer-antibody complex is excited with linearly polarized light, the emitted light remains highly polarized because the fluorophore is constrained from rotating between the time light is absorbed and emitted. When a "free" tracer compound (i.e., unbound to an antibody) is excited by linearly polarized light, its rotation is much faster than the corresponding tracer-antibody conjugate and the molecules are more randomly oriented, therefore, the emitted light is depolarized. Thus, fluorescent polarization provides a quantitative means for measuring the amount of tracer-antibody conjugate produced in a competitive binding immunoassay.

U.S. Pat. Nos. 4,510, 251 and 4,614,823, to Kirkemo et al., disclose fluorescent polarization assays for ligands using aminomethylfluorescein derivatives as tracers, and the aminomethylfluorescein derivatives, respectively. U.S. Pat. No. 4,476,229, to Fino et al., discloses substituted carboxyfluoresceins, including those containing a thyroxine analog, for use in fluorescence polarization immunoassays. U.S. Pat. No. 4,668,640, to Wang et al., discloses fluorescence polarization immunoassay utilizing substituted carboxyfluoresceins. Example IX of Wang et al. discloses a method for making a L-thyroxinecarboxyfluorescein conjugate of the following formula:

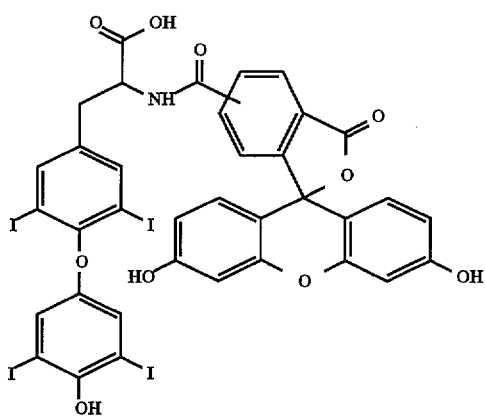

Both the Wang et al. and Fino et al. patents present a conjugate in which a carboxyfluorescein is directly attached to the amino group of the thyroxine via an amide bond.

Examples of commercially available fluorescence polarization immunoassays (FPIA) for thyroxine are: IMx®, TDx®, and TDxFLx™ T₄ assays (Abbott Laboratories, Abbott Park, Ill. Hereinafter also referred to as the "commercially available Abbott T₄ assay(s)" or "commercially available T₄ assay(s)") which include reagent systems for the quantitative measurement of total (i.e. free and protein bound) thyroxine present in a serum or plasma sample. All of these assays use the same fluorescent T₄ derivative as a tracer, which is labelled with a carboxyfluorescein (hereinafter also referred to as the "commercially available T₄ tracer" or "commercially available tracer"); the same sheep polyclonal antibodies against thyroxine (hereinafter also referred to as "commercially available T₄ antibodies", or "commercially available antibodies"); and the same reagent for removing the protein from the protein bound thyroxine in order to release the thyroxine for assay.

FPIAs have an advantage over radioimmunoassay (RIA) in that there are no radioactive substances to dispose of and FPIAs are homogenous assays that can be easily performed. However, it has been reported that the commercially available Abbott TDx® T₄ assay showed a low level of T₄ which did not conform to radioimmunoassay measurement and the clinical symptoms of hypothyroidism. See Levine, S. et al., *Clin. Chem.*, 36 (10): 1838–1840 (1990).

SUMMARY OF THE INVENTION

The present invention provides unique antibody reagents and labelled reagents for the quantification of thyroxine in a test sample. The present invention also provides synthetic procedures for preparing the labelled reagents, and for preparing immunogens which are employed for the production of the antibody reagents. According to the present invention, the labelled reagents and the antibody reagents offer an advance in the art beyond previously known procedures when used in an immunoassay for the quantification of thyroxine in a test sample. According to a preferred embodiment of the present invention, the labelled reagent and the antibody reagent are used in a fluorescence polarization immunoassay which combines specificity with the speed and convenience of homogeneous methods to provide a reliable quantification of thyroxine in a test sample and to avoid interference from endogenous immunoglobulin G (hereinafter referred to as "IgG") produced by some humans.

BRIEF DESCRIPTION OF THE DRAWINGS

FIG. 1 illustrates the synthetic pathway for making an immunogen of the present invention by coupling L-thyroxine to bovine serum albumin (BSA) according to the synthetic method of the present invention.

FIG. 2 illustrates the synthetic pathway for the preparation of a fluorescent tracer of the present invention according to the synthetic method of the present invention.

DETAILED DESCRIPTION OF THE INVENTION

According to the present invention, the specific quantification of thyroxine is accomplished by first contacting a test sample with a labelled reagent or tracer and an antibody reagent, either simultaneously or sequentially in either order, and then measuring the amount of the labelled-reagent which either has or has not participated in a binding reaction with the antibody reagent as a function of the amount of thyroxine in the test sample.

The test sample can be any naturally occurring body fluid or tissue, or an extract or dilution thereof, and includes, but is not intended to be limited to whole blood, serum, plasma, urine, saliva, cerebrospinal fluid, brain tissue, feces, and the like.

In particular, the present invention relates to immunogens, antibodies prepared from such immunogens, and labelled reagents for use in fluorescence polarization immunoassays (FPIA) for the specific quantification of thyroxine.

Throughout this application, the chemical structures shown in the formulae can be either the L or D isomer or a combination of L and D isomers. However, in all the formulae, L isomers are the most preferred.

Antibodies, both polyclonal and monoclonal antibodies, of the present invention are produced with immunogens of the following general formula:

FORMULA 2.
GENERAL STRUCTURE OF THE IMMUNOGEN

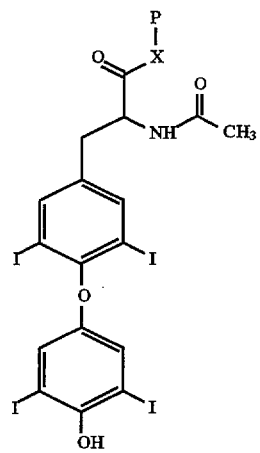

wherein P is an immunogenic carrier material and X is a linking moiety. The terms linking moeity, tether, spacer, spacer arm, and linker are used interchangeably and are meant to define any covalently bound chemical entity that separates one defined substance (such as a hapten) from a second defined substance (such as an immunogenic carrier or detectable moiety).

In the present invention, X is a linking moiety preferably consisting of from 0 to 50 carbon and heteroatoms, including not more than ten heteroatoms, arranged in a straight or branched chain or cyclic moiety or any combination thereof, saturated or unsaturated, with the provisos that: (1) not more than two heteroatoms may be directly linked, (2) X cannot contain —O—O—linkages, (3) the cyclic moieties contain 6 or fewer members, and (4) branching may occur only on carbon atoms. Heteroatoms may include nitrogen, oxygen, sulfur and phosphorous. Examples of X are: alkylene, aralkylene and alkylene substituted cycloalkylene groups. It shall be noted that, according to the definition herein, X can be zero, i.e. when the carbon and heteroatom are zero. If X=0, then no linking moiety exists, which indicates that P is directly linked to the thyroxine derivative in Formula 2.

As would be understood by one skilled in the art, the immunogenic carrier material P, can be selected from any of those conventionally known in the art, and in most instances will be a protein or polypeptide, although other materials such as carbohydrates, polysaccharides, lipopolysaccharides, poly(amino) acids, nucleic acids, and the like, of sufficient size and immunogenicity can also be employed. Preferably, the immunogenic carrier material is a protein such as bovine serum albumin (BSA), keyhole limpet hemocyanin (KLH), thyroglobulin, and the like.

In the preferred immunogen, P is bovine serum albumin (BSA) and X is —NH(CH$_2$)$_5$ C(=O)—. The preferred immunogen is shown below:

FORMULA 3
STRUCTURE OF THE PREFERRED THYROXINE IMMUNOGEN

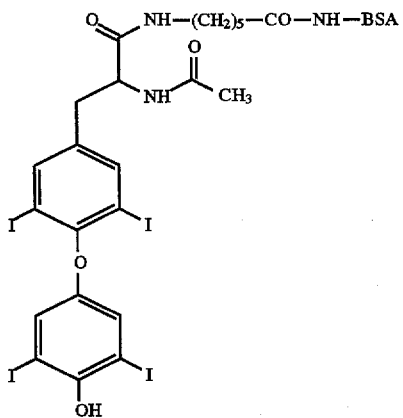

The most preferred thyroxine immunogen is the L isomer of Formula 3. The Formulae 2 and 3 are not limited to one to one conjugates of thyroxine and the immunogenic carrier, as one skilled in the art would realize. The ratio of thyroxine derivative to immunogenic carrier is defined by the number of chemically available functional groups on the immunogenic carrier and controlled by the ratio of the two materials in the synthesis. The degree of substitution on P by the thyroxine derivative can vary between 1 to 100% of the available functional groups on the immunogenic carrier. The level of substitution is preferably between 10% to 95%; and more preferably, between 15% to 85%.

Labelled reagents of the present invention have the following general formula:

FORMULA 4
GENERAL STRUCTURE OF THE LABELLED REAGENT

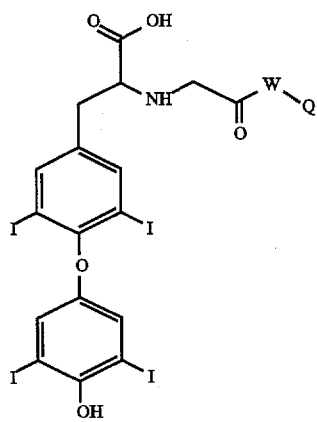

wherein Q is a detectable moiety, preferably a fluorescent moiety; and W is a linking moiety. In the preferred labelled reagent, Q is a fluorescein derivative chosen from the group consisting of 4'-aminomethylfluorescein, 5-aminomethylfluorescein, 6-aminomethyifluorescein, 5-carboxyfluorescein, 6-carboxyfluorescein, 5 and 6-aminofluorescein, thioureafluorescein, and methoxytriazinolyl-aminofluorescein. W is a linking moiety preferably consisting of from 0 to 50 carbon and heteroatoms, including not more than ten heteroatoms, arranged in a straight or branched chain or cyclic moiety or any combination thereof, saturated or unsaturated, with the provisos that: (1) not more than two heteroatoms may be directly linked, (2) W cannot contain —O—O-linkages, (3) the cyclic moieties contain 6 or fewer members, and (4) branching may occur only on carbon atoms. Heteroatoms may include nitrogen, oxygen, sulfur and phosphorous. The specific chemical structure of W can be the same or different from that of the X of Formula 2. Examples of W are: alkylene, aralkylene and alkylene substituted cycloalkylene groups. It shall be noted that, according to the definition herein, W can be zero, i.e. when the carbon and heteroatom are zero. If W=0, then no linking moiety exists, which indicates that Q is directly linked to the thyroxine derivative in Formula 4.

The preferred labelled reagent is of the following formula:

FORMULA 5
STRUCTURE OF THE PREFERRED THYROXINE TRACER

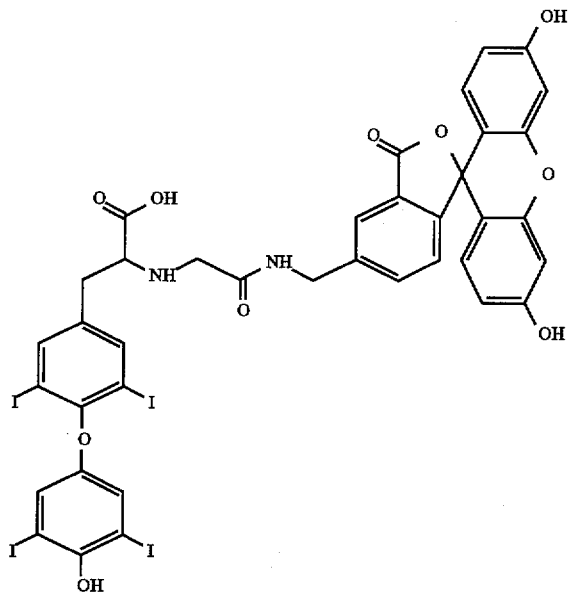

The most preferred labelled reagent is the L isomer of Formula 5. An example of a process for preparing the 5 methyl-substituted fluorescein derivative of Formula 5 is disclosed in U.S. patent application Ser. No. 859,775, of P. G. Mattingly, filed Mar. 30, 1992, entitled "5(6)-Methyl Substituted Fluorescein Derivatives" which is incorporated herein by reference.

The present invention has a surprising feature. It is known to one of ordinary skill in the art that when preparing specific antibodies and complementary labelled haptens (as the labelled reagents), one needs to consider the chemical structure of both the immunogen used to elicit the antibody response and the labelled hapten. Traditionally, one attaches the hapten to the carrier protein through a site on the hapten that is remote from the unique features of the hapten that are critical for achieving selective antibodies. Likewise, when preparing a labelled hapten able to bind to such antibodies, it is customary to attach the label to the hapten through the same site as the carrier protein. One reason behind such an approach is that the carrier protein may sterically block access of the immune system to that part of the hapten. Normally, the complementary labelled hapten is synthesized by attaching its label to the same site on the hapten as the immunogen uses for attachment of its carrier protein, so as not to interfere with antibody binding to the critical features of the hapten.

Therefore, it is surprising and unexpected to find that the thyroxine immunogen and labelled thyroxine of the present invention, which were derived from different sites of attachment on thyroxine, lead to development of specific antibodies to thyroine and an excellent assay with improved quantification of thyroxine.

Specifically, in the present invention, the immunogen was prepared from a thyroxine molecule which was conjugated to the carrier protein via the carboxylic acid terminal of thyroxine; whereas the labelled thyroxine reagent was prepared by attachment of the label at the amino terminal of thyroxine.

Additionally, as mentioned in the "Background of the Invention", the Wang et al. and Fino et al. patents present a conjugate in which a carboxyfluorescein is directly attached to the amino group of the thyroxine via an amide bond. In the current invention, the detectable moiety is attached, via a linking moiety to N-carboxymethyl-L-thyroxine, wherein the original amino group of the thyroxine is a secondary amine, not an amide. Further, unlike Wang et al and Fino et al., the synthetic method of the current invention requires a multistep treatment of thyroxine which makes extensive use of orthogonal protecting groups to arrive at the desired structure.

Preparation of the Immunogen

The general structure of the immunogen is as shown in Formula 2, where X is a linking moiety and P is an immunogenic carrier. Immunogens of Formula 2 may be produced according to the following scheme:

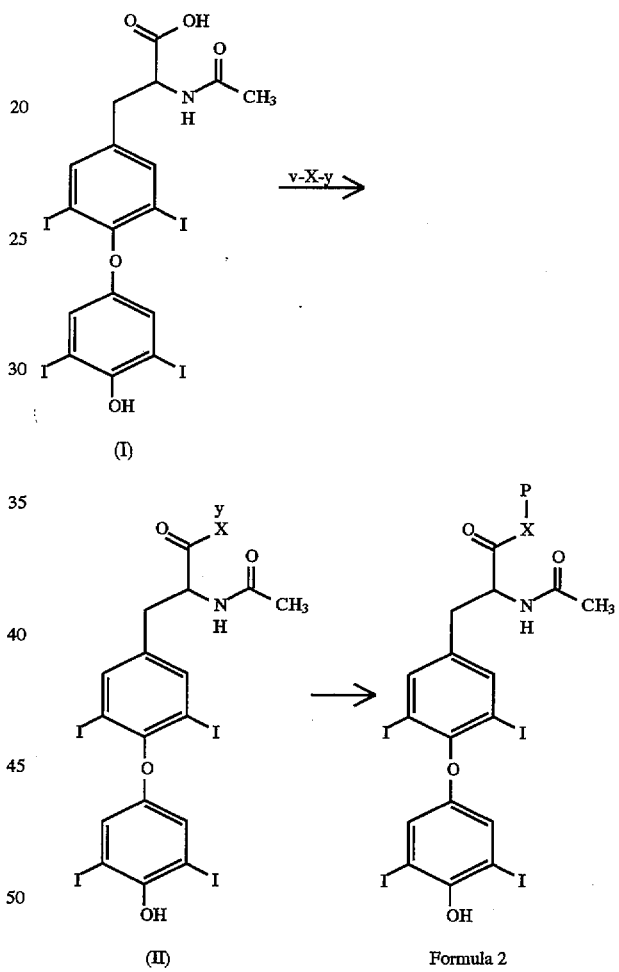

The N-acetyl-L-thyroxine (I) is coupled, according to methods known to those skilled in the art, with a bifunctional linker designated v-X-y wherein v- and -y are functional groups, one of which can react with the carboxylate of N-acetyl-L-thyroxine (I) and the other with chemically available functional groups on P. X is the linking moiety. Many bifunctional linkers are known to one skilled in this art. For example, heterobifunctional linkers are described in U.S. Pat. No. 5,002,883 to Bieniarz, et al, hereby incorporated by reference. These heterobifunctional linkers are preferred in some cases due to the specificity of their ends for one functional group or another. Likewise, for convenience in the synthesis, protected forms of the functional groups v- and -y, well known to those skilled in the art (see e.g. T. W. Greene and P. G. M. Wutts, *Protective Groups in Organic Synthesis*, 2nd ed. 1991, John Wiley and Sons, hereby incorporated by reference) may be used and deprotected at the desired time.

Generally, in the preparation of immunogens of the present invention, v is selected from the group consisting of: —OH, -halogen (e.g. —Cl, —Br, —I), —SH, and —NHR'—. R' is selected from H; alkyl, aryl, substituted alkyl and substituted aryl; y is chosen from the group consisting of: hydroxy (—OH), carboxy (—C(=O)OH), amino (—$NH_2$), aldehyde (—CH(=O)), and azido (—$N_3$). X is a linking moiety preferably consisting of from 0 to 50 carbon and heteroatoms, including not more than ten heteroatoms, arranged in a straight or branched chain or cyclic moiety or any combination thereof, saturated or unsaturated, with the provisos that: (1) not more than two heteroatoms may be directly linked, (2) X cannot contain —O—linkages, (3) the cyclic moieties contain 6 or fewer members, and (4) branching may occur only on carbon atoms. Heteroatoms may include nitrogen, oxygen, sulfur and phosphorous. Examples of X are: alkylene, aralkylene and alkylene substituted cycloalkylene groups. It shall be noted that, according to the definition herein, X can be zero, i.e. the carbon and heteroatom are zero. If X=0, then no linking moiety exists, which indicates that P is directly linked to the thyroxine derivative in Formula 2.

Reaction of the N-acetyl-L-thyroxine (5) with v-X-y produces tethered intermediate compound (II) having linking moiety X with a functional group y. The functional group -y, can be reacted in any of several ways, known to those skilled in the art, with the functional groups on an immunogenic carrier. It is frequently preferable to form amide bonds, which typically are quite stable. Amide bonds are formed by first activating the carboxylic acid moiety [y= (—C(=O)OH)] of the spacer arm by reaction with an activating reagent such as 1,3-dicyclohexylcarbodiimide and an additive such as N-hydroxysuccinimide. The activated form is then reacted with a buffered solution containing the immunogenic carrier materials. Alternatively, the carboxylic acid group may be converted, with or without isolation, into a highly reactive mixed anthydride, acyl halide, acyl imidazolide, or mixed carbonate and then combined with the immunogenic carrier materials. One of ordinary skill in the art will recognize that there are many reagents that can be used to form amide bonds other than those listed.

A spacer arm with a terminal amine (y=—$NH_2$) functionality can be transformed into a highly reactive N-hydroxysuccinimide urethane by reaction with N,N'-disuccinimidyl carbonate in a suitable solvent, such as acetonitrile or dimethylformamide. The resultant urethane is then reacted with the immunogenic carrier materials in a buffered, aqueous solution to provide an immunogen.

A spacer arm with a terminal aldehyde functionality [y=—CH(=O)] can be coupled to the immunogenic carrier materials in a buffered, aqueous solution and in the presence of sodium cyanoborohydride, by reductive amination according to methods known to those skilled in the art.

Alternatively, spacer arms containing an alcohol group [y=—OH] can be coupled to the immunogenic carrier materials by first reacting it with phosgene or phosgene equivalent, such as di or triphosgene or carbonyldiimidazole, resulting in the formation of a highly reactive chloroformate or imidazoloformate derivative (usually without isolation). The resultant active formate ester is then reacted with the immunogenic carrier materials in a buffered, aqueous solution to provide an immunogen.

Alternatively, when y=—$N_3$, the tethered intermediate can be coupled to P by photolysis in aqueous buffered solution.

The preferred immunogen of Formula 3 is thus prepared according to the scheme of FIG. 1. L-thyroxine (1) sodium salt is converted to N-acetyl-L-thyroxine (5); the carboxyl group of N-acetyl-L-thyroxine (5) is activated with dicylcohexylcarbodiimide and N-hydroxysuccinimide (the boldfaced numerals contained in parenthesis refer to the structural formulae used in FIG. 1). Further reaction with the linker, 6-aminocaproic acid [v=—$NH_2$, X=—$(CH_2)_5$-, y=—$CO_2H$] gives the tethered intermediate [6, X=— $(CH_2)_5$-, y=—$CO_2H$]. The y-group is then activated with dicylcohexylcarbodiimide and N-hydroxysuccinimide and coupled to P. Those skilled in the art will recognize that other methods for peptide bond formation could be employed with equal success.

In a manner analogous to immunogens, spacer arms can be conjugated to solid supports having functional groups such as amino, hydroxyl or carboxyl groups that are reactive in a complementary sense with reactive groups on the spacer arm. The result is a solid phase which can be used to separate or purify antibodies against the hapten.

Thus the above thyroxine derivatives can be coupled to immunogenic carrier materials P by various conventional techniques known in the art.

Production of Antibodies

The immunogens according to the present invention are used to prepare antibodies, both polyclonal and monoclonal, according to methods known in the art, for use in an immunoassay system according to the present invention. Generally, a host animal, such as a rabbit, goat, mouse, guinea pig, or horse is injected at one or more of a variety of sites with the immunogen, normally in a mixture with an adjuvant. Further injections are made at the same site or different sites at regular or irregular intervals thereafter with bleedings being taken to assess antibody titer until it is determined that optimal titer has been reached. The antibodies are obtained by either bleeding the host animal to yield a volume of antiserum, or by somatic cell hybridization techniques or other techniques known in the art to obtain monoclonal antibodies, and can be stored, for example, at −20° C. Besides whole immunoglobulins, antibodies herein include antigen binding fragments of the immunoglobulins. Examples of these fragments are Fab, F(ab')$_2$ and Fv. Such fragments can be produced by known methods.

It is to be noted from Example 4 that the replacement of the commercially available $T_4$ tracer with the labelled reagent of the present invention alone improves the performance of a thyroxine assay. Thus, the assays or kits can use the labelled reagents of the present invention with antibodies, whether polyclonal or monoclonal, which recognize both thyroxine and the labelled reagents, and which are preferably antibodies that are raised by the immunogens of Formulae 2 and 3. Additionally, to enable the performance of competitive immunoassays such as FPIA, the tracers and thyroxine must be able to competitively bind to the antibodies. Since the test samples would mostly be biological samples, though the antibodies may bind both isomers of thyroxine, it is preferable that the antibodies preferably bind L-thyroxine. Similarly, the immunogens are preferably derivatives or analogs of L-thyroxine. The labelled reagents preferably do not bind or significantly bind endogenous immunoglobulins which may be found in the test sample, i.e. antibodies that are not intended to bind the labelled reagents, such that the binding interferes with the accuracy of the assay. In Example 4 below, these immunoglobulins are immunoglobulins G (IgG).

Preparation of the Labelled Reagent

The following describes the method for synthesizing the labelled reagents of the present invention. These labelled reagents can be synthesized from thyroxine by: (a) differentially protecting the carboxylic acid, α-amino and phenolic groups of thyroxine (according to the method as shown in, e.g. T. W. Greene and P. G. M. Wutts, *Protective Groups in Organic Synthesis*, 2nd ed. 1991, John Wiley and Sons, hereby incorporated by reference); then (b) selectively deprotecting the α-amino group of the thyroxine derivative; next (c) selectively carbalkoxymethylating the α-amino group; followed by (d) selectively deprotecting the α-N-carboxymethyl group and the phenolic group of the thyroxine derivative; then (e) activating the α-N-carboxymethyl group; next (f) coupling the activated α-N-carboxymethyl group of the thyroxine derivative with a bifunctional linking moiety, then (g) coupling with a detectable moiety; and finally (h) deprotecting the carboxylic acid group of the labelled reagent. One skilled in the art would also recognize that steps f and g could be combined; the detactable moiety could be coupled to the bifunctional linking moiety before coupling to the thyroxine derivative of step e.

More specifically, the labelled reagent can be synthesized by: (a) (i) reacting a sodium salt of thyroxine with 9-fluorenylmethoxycarbonyl chloride (FMOC-Cl) to protect the amino group followed by (ii) protecting the phenolic functionality of the resulting thyroxine derivative by acetylation, then (iii) protecting the carboxylic group of the N-FMOC-O-acetyl-thyroxine as the tert-butyl ester; followed by (b) removing the FMOC protective group to give t-butyl O-acetyl-thyroxine; next (c) alkylating areinc group of t-butyl O-acetyl-thyroxine with bromoacetic acid ethyl ester to give t-butyl O-acetyl-N-carboethoxymethyl-thyroxine; then (d) hydrolysing the ethyl ester and acetyl groups of t-butyl O-acetyl-N-carboethoxymethyl-thyroxine with sodium hydroxide in methanol and obtaining t-butyl N-carboxymethyl-thyroxine in the same process; and (e) activating the t-butyl N-carboxymethyl-thyroxine with dicylcohexylcarbodiimide and N-hydroxysuccinimide; then (f) reacting the thyroxine derivative with 5-aminomethylfluorescein to give t-butyl N-(5-carboxamidomethylfluoresceinyl-methyl)-thyroxine; followed by (g) hydrolysing the t-butyl ester with trifluoroacetic acid to give the labelled reagent. This method is exemplified in the synthesis of the preferred labelled reagent as shown in FIG. 2.

Preferably, the above synthetic methods am used to produce the labelled reagents of Formulae 4 and 5, and more preferably the L structures of these formulae.

Thyroxine Assay Utilizing Fluorescence Polarization Immunoassay

The concentration or level of thyroxine in a test sample can be accurately quantified in a fluorescence polarization immunoassay (FPIA) by employing the reagents of the present invention. To perform a FPIA for the specific quantification of thyroxine, calibration curves using known amount, of thyroxine were generated for measuring the thyroxine in a sample.

According to the present invention, it has been unexpectedly and surprisingly found that superior fluorescence polarization immunoassay assay results for the quantification of thyroxine are obtained when employing the L isomer of the fluorescent labelled reagent (or tracer) of Formula 5.

In particular, it was unexpectedly and surprisingly found that the use of this labelled reagent was critical for the avoidance of discrepant results. This represents an advance over the commercially available Abbott $T_4$ assays for the specific quantification of thyroxine. More generally, the tracer can be of Formula 4. When performing a fluorescence polarization immunoassay for the specific quantification of thyroxine as described herein, the detectable moiety component of the tracer is a fluorescent moiety such as fluorescein, aminofluorescein, carboxyfluorescein, and the like, preferably 5 and 6-aminomethylfluorescein, 5 and 6-aminofluorescein, 6-carboxyfluorescein, 5-carboxyfluorescein, thioureafluorescein, and methoxytriazinolyl-aminofluorescein, and similar fluorescent derivatives. The fluorescent tracer can be used in combination with an antibody which is capable of binding both the tracer and $T_4$. For a competitive immunoassay the tracer and $T_4$ must be able to competitively bind to the antibody. For the quantification of thyroxine, the antibody reagent comprises antibodies which are capable of binding to or recognizing thyroxine wherein the antibodies are preferably produced with an immunogen of Formula 2, and more preferably that of Formula 3.

The amount of tracer bound to the antibody varies inversely to the amount of thyroxine present in the test sample. Accordingly, the relative binding affinities of thyroxine and the tracer to the antibody binding site are important parameters of the assay system.

Generally, fluorescent polarization techniques are based on the principle that a fluorescent tracer, when excited by plane polarized light of a characteristic wavelength, will emit light at another characteristic wavelength (i.e., fluorescence) that retains a degree of the polarization relative to the incident stimulating light that is inversely related to the rate of rotation of the tracer in a given medium. As a consequence of this property, a tracer substance with constrained rotation, such as in a viscous solution phase or when bound to another solution component such as an antibody with a relatively lower rate of rotation, will retain a relatively greater degree of polarization of emitted light than if in free solution.

When performing a fluorescent polarization immunoassay for the specific quantification of thyroxine according to the present invention, a test sample suspected of containing thyroxine is contacted with antiserum or monoclonal antibodies prepared with immunogens according to the present invention, in the presence of labelled reagent of the present invention, which is capable of producing a detectable fluorescence polarization response to the presence of antiserum or monoclonal antibodies prepared with immunogens according to the present invention. Plane polarized light is then passed through the solution to obtain a fluorescent polarization response and the response is detected as a measure of amount of thyroxine present in the test sample.

The thyroxine derivatives of the present invention are employed to prepare immunogens by coupling them to conventional carrier materials, and subsequently used to obtain antibodies. The thyroxine derivatives of the present invention are also used to prepare labelled reagents which serve as the detection reagents in immunoassays for quantifying thyroxine in a test sample.

The fluorescence polarization assays can be conducted in commercially available automated instruments such as: IMx®, TDx®, and TDxFLx™ (Abbott Laboratories).

Other Assay Formats

In addition to fluorescence polarization immunoassays, various other immunoassay formats can be followed for the quantification of thyroxine according to the present invention. Such immunoassay system formats include, but are not limited to competitive and sandwich assay techniques. Generally, such immunoassay systems depend upon the ability of an immunoglobulin, i.e., a whole antibody or fragment thereof, to bind to a specific analyte from a test sample wherein a labelled reagent comprising an antibody of the present invention, or fragment thereof, attached to a label or detectable moiety is employed to determine the extent of binding. Such labels or detectable moieties include, but are not intended to be limited to, enzymes, radiolabels, biotin, toxins, drugs, haptens, DNA, RNA, liposomes, chromophores, chemiluminescens, colored particles and colored microparticles, fluorescent compounds such as aminomethylfluorescein, 5-carboxyfluorescein, 6-carboxyfluorescein, aminofluorescein, thioureafluorescein, and methoxytriazinolyl-aminofluorescein, and the like fluorescent derivatives.

Typically, the extent of binding in such immunoassay system formats is determined by the amount of the detectable moiety present in the labelled reagent which either has or has not participated in a binding reaction with the analyte, wherein the amount of the detectable moiety detected and measured can be correlated to the amount of analyte present in the test sample. For example, in a competitive immunoassay system, a substance being measured, often referred to as a ligand, competes with a substance of close structural similarity coupled to a detectable moiety, often referred to as a tracer, for a limited number of binding sites on antibodies specific to the portion or portions of the ligand and tracer with structural similarity. These binding sites are usually shared with an immunogen employed to produce such antibodies.

Test Kits

A test kit according to the present invention comprises all of the essential reagents required to perform a desired specific fluorescence polarization immunoassay according to the present invention for the quantification of thyroxine in a test sample. The test kit is presented in a commercially packaged form as a combination of one or more containers holding the necessary reagents, as a composition or admixture where the compatibility of the reagents will allow.

Particularly preferred is a test kit for the fluorescent polarization immunoassay quantification of thyroxine in a test sample, comprising fluorescent tracer compounds and antibodies as described above for the quantification of thyroxine. It is to be understood that the test kit can, of course, include other materials as are known in the art and which may be desirable from a user standpoint, such as buffers, diluents, standards, and the like.

The present invention will now be illustrated, but is not intended to be limited by, the following examples. In Examples 1 and 2, the bold-faced numerals contained in parenthesis refer to the structural formulae as used in FIGS. 1 and 2, respectively:

EXAMPLE 1

SYNTHESIS OF THE L-THYROXINE IMMUNOGEN (7)

Abbreviations: EtOH=ethanol, $NH_4OH$=ammonium hydroxide, HCl=hydrochloric acid, DMF= dimethylformamide, NaOH=sodium hydroxide, THF= tetrahydrofuran, $CH_2Cl_2$=methylene chloride, MEOH= methanol, HOAc=acetic acid.

L-Thyroxine sodium salt, pentahydrate (1)(10 g, 11 mmol) was nearly completely dissolved in 400 mL of EtOH/2 N $NH_4OH$ (1/1, v/v), filtered, and filtrate poured into 425 mL of 5% HCl. The resulting precipitate was isolated by vacuum filtration and dried under high vacuum to afford a white solid. This material was dissolved in 160 mL DMF, 100 mL (1.06 mol) of acetic anhydride added, and reaction stirred for 1.5 hours, then diluted with 850 mL $H_2O$ and allowed to stand at 4° C. for 16 hours. The resulting precipitate was isolated by filtration, then dissolved in 350 mL EtOH and 41 mL of 1N NaOH, stirred for 2.5 hours, 680 mL of 5% HCl added, and mixture allowed to stand at 4° C. for 16 hours. The resulting precipitate was isolated by vacuum filtration and dried under high vacuum to yield 8.1 g (90%) of the desired N-acetyl L-thyroxine (5) as a white solid; $^1$H NMR (200 MHz, $CD_3OD$) d 7.8 (s, 2H), 7.1 (s, 2H), 4.6–4.7 (m, 1H), 2.8–3.0 (m, 2H), 2.0 (s, 3H); mass spec (FAB) (M+H)+820.

N-Acetyl L-thyroxine (5) (1.0 g, 1.2 mmol) was dissolved in 50 mL THF, 170 mg (1.5 mmol) of N-hydroxysuccinimide added, 300 mg (1.5 mmol) of 1,3-dicyclohexylcarbodiimide added, and reaction stirred under $N_2$ for 3 days. The reaction was then vacuum filtered to remove insoluble urea, affording 40 mL of filtrate. Half the filtrate volume (20 mL, 0.6 mmol) was combined with 80 mg (0.6 mmol) of 6-aminocaproic acid, reaction pH adjusted to 9 with triethylamine, and reaction allowed to stir under $N_2$ for 2 days. Solvent was then removed in vacuo and crude product purified by elution on a silica gel Chromatotron® (Harrison Research, Palo Alto, Calif.), eluting with $CH_2Cl_2$/MeOH/HOAc (90/10/0.2, v/v), to yield 300 mg (54%) of the desired product (6) as a yellow oil; Mass spec (FAB) (M+H)+933.

The acid (6) (300 mg, 0.322 mmol) was dissolved in 25 mL THF, 45 mg (0.39 mmol) of N-hydroxysuccinimide added, 80 mg (0.39 mmol) of 1,3-dicyclohexylcarbodiimide added, and the reaction mixture stirred for 16 hours under $N_2$. The reaction was then vacuum filtered to remove insoluble urea, affording 16 mL of filtrate. Then 4 mL (0.08 mmol) of the filtrate was added to a stirred solution of 250 mg (0.0037 mmol) of bovine serum albumin dissolved in 10 mL of 0.05M sodium phosphate (pH=8.0) and 10 mL DMF. After stirring for 3 days the reaction was dialyzed against 4 L of 0.05M sodium phosphate (pH=8.0) for 24 hours, then against 4 L of $H_2O$ for 24 hours, then lyophilized, to afford 297 mg of the desired L-thyroxine immunogen (7).

EXAMPLE 2

SYNTHESIS OF THE L-THYROXINE TRACER (4)

Abbreviations: THF=tetrahydrofuran, EtOAc=ethyl acetate, DMSO=dimethylsulfoxide, $CHCl_3$=chloroform, $CH_2Cl_2$=methylene chloride, MeOH=methanol, HOAc= acetic acid, Hex=hexane, DMF=dimethylformamide.

Sodium carbonate (7.85 g, 74.1 mmol) was dissolved in 480 mL $H_2O$, 480 mL THF added, 22.0 g (24.7 mmol) of L-thyroxine sodium salt, pentahydrate (1) added, 7.04 g (27.2 mmol) of 9-fluorenylmethyl chloroformate added, and reaction stirred for 30 minutes. The reaction was then diluted with 170 mL of 1M HCl and extracted with EtOAc (3×700 mL). The EtOAc extracts were combined, dried over $Na_2SO_4$, and solvent removed in vacuo to afford 26.3 g of the desired N-FMOC product as a beige solid; $^1$H NMR (300 MHz, DMSO-D6) d 9.29 (s,1H), 7.08–7.89 (m, 12H), 4.19–4.29 (m, 4H), 3.06–3.16 (m, 1H), 2.82 (t, 1H); mass spec (FAB) (M–H+Na)+1021.

The N-FMOC protected L-Thyroxine (26.3 g, 23.2 mmol) was dissolved in 150 mL THF, 3.28 mL (34.8 mmol) of acetic arthydride added, 283 mg (2.32 mmol) of 4-dimethylaminopyridine added, and reaction stirred under $N_2$ for 45 minutes, then poured into 400 mL $H_2O$ and extracted with $CHCl_3$ (3×400 mL). The $CHCl_3$ extracts were combined, dried over $Na_2SO_4$, and solvent removed in vacuo. The residue was then purified by silica gel column chromatography, eluting with $CH_2Cl_2$/MeOH/HOAc (90/10/0.4, v/v), to yield 21.95 g (91%) of the desired O-acetyl thyroxine as a beige solid; $^1$H NMR (300 MHz, DMSO-D6) d 7.12–7.91 (m, 12H), 4.07–4.31 (m, 4H), 3.07–3.19 (m, 1H), 2.82 (t, 1H), 2.29–2.40 (m, 3H); mass spec (FAB) (M+H)+1042.

The N-FMOC, O-acetyl L-thyroxine (21.70 g, 19.17 mmol) was dissolved in 250 mL $CH_2Cl_2$, cooled to 0° C., and 19.20 g (95.85 mmol) of O-t-butyl-N,N'-diisopropylisourea in 50 mL $CH_2Cl_2$ added in a dropwise fashion. The reaction was then stirred overnight, under $N_2$, at room temperature, then vacuum filtered to remove insoluble impurities, and filtrate solvent removed in vacuo. The resulting residue was stirred in 300 mL of EtOAc/Hex (40/60, v/v) for 4 hours, vacuum filtered to remove insoluble impurities, and filtrate solvent removed in vacuo. The residue was then purified by silica gel column chromatography, eluting with EtOAc/Hex (40/60, v/v), to afford 9.64 g (46%) of the desired t-butyl ester (2) as a beige solid; $^1H$ NMR (300 MHz, $CDCl_3$) d 7.18–7.82 (m, 12H), 4.21–4.57 (m, 4H), 3.05 (s, 2H), 2.39 (s, 3H), 1.33–1.54 (m, 9H); mass spec (FAB) (M+H)+1098.

N-FMOC, O-Acetate L-thyroxine t-butyl ester (2) (9.59 g, 8.04 mmol) was dissolved in 40 mL DMF, 1.12 mL (8.04 mmol) of triethylamine added, and reaction stirred overnight, under $N_2$. Then 1.78 mL (16.1 mmol) of ethyl bromoacetate was added, followed by another 1.12 mL (8.04 mmol) of triethylamine, and reaction stirred an additional 2 hours under $N_2$, then poured into 200 mL $H_2O$ and extracted with EtOAc (3×200 mL). The EtOAc extracts were combined, dried over $MgSO_4$, and solvent removed in vacuo. The resulting oil was purified initially by silica gel column chromatography, eluting with EtOAc/Hex (40/60, v/v), and then purified a second time by preparative silica gel HPLC, eluting with EtOAc/Hex (20/80, v/v), to yield 3.77 g (49%) of the desired N-carboxymethyl ethyl ester derivative as a white solid; $^1H$ NMR (300 MHz, $CDCl_3$) d 7.75 (s, 2H), 7.19 (s, 2H), 4.20 (q, 2H), 3.39–3.49 (m, 3H), 2.80–2.98 (m, 2H), 2.39 (s, 3H), 1.42 (s, 9H), 1.27 (t, 3H); mass spec (FAB) (M+H)+962.

The ethyl ester intermediate (3.73 g, 3.88 mmol) was dissolved in 85 mL MeOH, 12.4 mL (31 mmol) of 10% sodium hydroxide added, and reaction stirred for 40 minutes. The reaction was then poured into 250 mL $H_2O$, pH adjusted to 4 with 1M HCl, and extracted with EtOAc (3×250 mL). The EtOAc extracts were combined, dried over $MgSO_4$, and solvent removed in vacuo to afford 3.29 g (95%) of the desired product (3) as a white solid; $^1H$ NMR (300 MHz, DMSO-D6) d 7.81 (s, 2H), 7.07 (s,.2H), 3.52 (t, 1H), 3.32 (s, 2H), 2.89–2.98 (m, 1H), 2.20–2.31 (m, 1H), 1.32 (s, 9H); mass spec (FAB) (M+H)+892.

The free acid (3) (1.78 g, 2.00 mmol) was dissolved in 20 mL DMF, 230 mg (2.00 mmol) of N-hydroxysuccinimide added, 413 mg (2.00 mmol) of 1,3-dicyclohexyicarbodiimide added, and reaction stirred for 16 hours, under $N_2$. The reaction was then vacuum filtered, filtrate combined with 884 mg (2.00 mmol) of 5-aminomethylfluorescein hydrobromide and 1.8 mL (13 mmol) of triethylamine, and the reaction stirred for 16 hours, under $N_2$, in the dark, then solvent removed in vacuo. The residue was purified by preparative reverse phase $C_{18}$ HPLC, eluting with $H_2O$/MeOH/HOAc (25/75/0.4, v/v), to afford 1.51 g (61%) of the desired t-butyl ester protected tracer as an orange solid; $^1H$ NMR (300 MHz, DMSO-D6) d 10.13 (s, 2H), 9.29 (s, 1H), 8.43 (t, 1H), 7.85 (s, 1H), 7.83 (s, 2H), 7.68 (d, 1H), 7.12–7.28 (m, 2H), 7.07 (s,. 2H), 6.68 (s, 2H), 6.54 (s, 4H), 4.36–4.61 (m, 2H), 3.26–3.50 (m, 3H), 2.94–3.04 (m, 1H), 2.71–2.82 (m, 1H), 1.33 (s, 9H); mass spec (FAB) (M)+ 1234.

The t-butyl ester tracer (1.464 g, 1.19 mmol) was dissolved in 30 mL of $CH_2Cl_2$,trifluoroacetic acid (1/1, v/v), stirred for 5 hours, and solvent removed in vacuo. The crude product was purified by preparative reverse phase $C_{18}$ HPLC, eluting with $H_2O$/MeOH/HOAc (25/75/0.4, v/v) to yield 1.01 g (72%) of the desired L-thyroxine tracer (4) as an orange solid; $^1H$ NMR (300 MHz, DMSO-D6) d 10.0–10.3 (broad s, 2H), 8.31 (t, 1H), 7.86 (s, 2H), 7.83 (s, 1H), 7.64 (d, 1H), 7.15–7.30 (m, 2H), 7.08 (s, 2H), 6.68 (s, 2H), 6.55 (s, 4H), 4.31–4.59 (m, 2H), 3.28–3.55 (m, 3H), 2.82–2.99 (m, 2H); mass spec (FAB) (M+H)+1179.

EXAMPLE 3

ANTIBODY PRODUCTION

Immunization Strategy

A 2 ml slurry mixture containing 1.0 mg of the lyophilized immunogen, as described in Example 1, in physiological buffered saline (catalog no. #NDC 007-7983-02, Abbott Laboratories, Abbott Park, Ill., was added to MPL+TDM adjuvant solution as contained in a vial provided by the manufacturer (catalog no. #R-700, RIBI Immunochem Research, Inc., Hamilton Mont.) and vigorously vortexed for 3 minutes. Fifteen mice of strain BCF1 (Jackson Laboratories, Bar Harbor, Me.) each received a 0.1 ml injection dispersed equally between subcutaneous and interperitoneal sites. This immunization strategy, repeated every 2 weeks for a total of 4 boosts was followed by collection of serum samples 2 weeks later. The bleed was allowed to incubate for 2 hours at room temperature before the sera was withdrawn and stored at –20° C. or colder.

Sera Evaluation

The serum Samples were tested on the TDx® instrument using the commercially available $T_4$ reagent pack (both from Abbott Laboratories, Abbott Park, Ill.) to determine the presence of antibody which could bind the commercially available TDx® $T_4$ tracer from the TDx® $T_4$ reagent pack (Catalog Code No. 97608, Abbott Laboratories) in a fluorescence polarization assay. The screening assay was essentially the same as described in the commercially available TDx® $T_4$ assay user manual except that the $T_4$ antibodies in the commercially available $T_4$ reagent pack were replaced with the commercially available TDx® diluent (Abbott Laboratories.). The serum samples to be tested were added to the sample well of the cartridge of the TDx® carousel. The serum samples were titrated in $log_2$ dilutions in the sample wells of the TDx® carousel. Nine of the mice produced antibodies which bind the commercially available TDx® T4 tracer. One of the animals, designated animal #12, was selected because its Net P (i.e. Net Polarization) signals were greater than the titrated normal mouse serum control from non-immunized mice (Catalog No. #5011-1380, lyophilized normal mouse serum, Cappel, Dunham, N.C.) by 60–80 mP. ("mP" denotes "millipolarization").

Fusion

Following a 5 month rest period, animal #12 was administered a 25 µg/ml interveneous pre-fusion boost 3 days prior to the fusion. On the day of the fusion, the animal was sacrificed and the splenocytes were washed one time in Iscove's Modified Dulbecco Medium (IMDM) (GIBCO, Grand Island, N.Y.) and centrifuged 1000 RPM for 10 minutes. The pelleted splenocytes were combined with SP2/0 myeloma cells (from the laboratory of Dr. Milstein, Cambridge, United Kingdom) at a 1:3 ratio, washed in IMDM, and centrifuged. The supernatant was removed and 1 ml of 50% PEG (i.e. polyethylene glycol) (American Type Culture Collection, Rockville, Md.) was added to the pellet for 1 minute as the pellet was gently being dispersed by tapping and swirling. Thirty mls of IMDM was added to the mixture and centrifuged as previously described. Supernate was decanted, the pellet was resuspended in IMDM with HAT (i.e. hypoxanthine aminopterin thymidine) (GIBCO), 10% FBS (i.e. fetal bovine serum) (Hyclone, Logan, Utah)

and 1% STM v/v (RIBI Immunochem Research, Inc.). STM denotes *Salmonella typhimurium* mitogen. The STM solution was added as a B-cell mitogen. The fusion cell suspension was plated into 96-well tissue culture plates.

Primary Fusion Screening

The primary screening of the fusion occurred on day 12 of confluent cultures. The Screen Machine (IDEXX, Portland, Me.) fluorescent concentrated particle immunoassay (FCPIA) utilizes goat anti-mouse microparticles to capture any mouse antibody secreted from the hybrids in supernate. The commercially available Abbott $T_4$ tracer (from the TDx® $T_4$ assay-reagent pack, Abbott Laboratories) was added to identify the antibodies which were $T_4$ reactive (i.e. bound $T_4$). Relative fluorescent intensity of hybrid #1-189 was 3 times that of the negative control (Catalog No. #5011-1380, lyophilized normal mouse serum, Cappel, Dunham, N.C.) and was selected as a candidate for further evaluation and cloning.

Hybrid Cloning

Hybrid #1-189 was cloned directly from the 96 well fusion plate by limiting dilutions starting at 1-100, 10-fold to $10^6$. The cloning media used was IMDM with 10% v/v FBS and 1% v/v HT (i.e. hypoxanthine thymidine) Supplement (GIBCO). 100 μl cell suspension was added to each of the 96 wells in the tissue culture plate. On day 7 the plates were fed with 200 μl/well of cloning media.

Clone Selection

Clone $T_{4\ 1}$-189-252 was selected for further evaluation based on the modified TDx® $T_4$ screen of the above "Sera evaluation" section. The polyclonal antisera in the $T_4$ reagent pack was replaced with commercially available TDx® diluent (Abbott Laboratories.). The clone supernate was added to the sample well of the cartridge of the TDx® carousel. In the pre-dilution well of the TDx® cartridge, duplicates of 0 and 24 μl/dl free $T_4$ were placed. The TDx® $T_4$ Plus assay (previously commercially available from Abbott Laboratories for the TDx® instrument, this assay measured the total circulating $T_4$ in a serum or plasma sample) was run (as described in the previously commercially available TDx® $T_4$ Plus assay user manual), and the monoclonal antibody samples which showed a decrease in polarization were selected for further evaluation. The decrease in polarization was due to the $T_4$ in the sample which competitively displaced the $T_4$-FITC from the monoclonal antibdody. For this experiment, the current commercially available TDx® $T_4$ assay (Abbott Laboratories, this assay also measures the total circulating $T_4$ in a serum or plasma sample) conducted according to its assay user manual, could be used in place of the TDx® $T_4$ Plus assay. The polyclonal antibodies and tracer used in the TDx® $T_4$ Plus assay are the same as those used in the TDx® $T_4$ assay.

Isotype

The isotype of the monoclonal antibody secreted from the cell line identified as $T_{4\ 1}$-189-252 was determined on an EIA clonotyping kit (Southern Biotech, Birmingham, Ala.). The assay was performed according to the vendor recommendations and the results indicated an isotype of IgG2a, kappa.

Isoelectric Focusing

The isoelectric point (pI) of the monoclonal antibody secreted from the cell line identified as $T_{4\ 1}$-189-252 is determined on an isoelectric focusing apparatus (Bio Rad, Richmond, Calif.). The gel was cast and run according to vendor recommendations. The results indicated pI=7.4±0.2.

Cell Line Deposit

The hybridoma cell line $T_{4\ 1}$-189-252 has been deposited with the American Type Culture Collection (ATCC), 12301 Parklawn Drive, Rockville, Md. 20852, U.S.A. in accordance with the Budapest Treaty. The deposit date is Sep. 16, 1992 and the ATCC number assigned to the cell line is HB 11125. The monoclonal antibody produced by this hybridoma is hereby referred to as monoclonal antibody 1-189-252.

EXAMPLE 4

FLUORESCENCE POLARIZATION IMMUNOASSAY FOR THYROXINE

Endogenous antibodies present in the serum samples of certain individuals cause falsely low total $T_4$ readings in the commercially available TDx®, TDxFLx™; and IMx® assays. These same samples, when evaluated by the RIA method, yield values consistent with clinical diagnosis. Evaluation of these serum samples demonstrated that a binding factor, an immunoglobulin, is present that has a high affinity for the commercially available Abbott $T_4$ tracer. This results in an increase in retention of polarization generating a high millipolarization units (mP) value, hence a low $T_4$ reading.

In the present invention, the tracer of Example 2 and monoclonal antibody 1-189-252 were optimized to perform as well as the commercially available Abbott $T_4$ FPIA, and it was discovered that this new assay has the additional advantage of avoiding the above discrepant readings. The new assay uses the same standard protocol and diluents as used in the commercially available assays. The results of the assay run are reported in millipolarization units (mP). The mP units are automatically interpolated from a stored standard curve and expressed as concentrations (microgram/dL) of thyroxine in the assayed samples. This procedure is the same for both the commercially available Abbott reagents and the new tracer and monoclonal antibody.

For example, in the case of the TDx® new $T_4$ assay, the samples were run according to the standard protocol on the TDx® analyzer. The efficacy of the TDx® new $T_4$ assay was evaluated by comparing it with the commercially available TDx® $T_4$ assay using 373 patient serum samples. Good agreement between the two assays for detecting $T_4$ was found. The new assay could detect between 0 to 24 μg/dL of thyroxine in a sample. Samples containing thyroxine concentrations greater than 24 μg/dL should be diluted first, for example, in accordance with the vendor's instruction for the commercially available TDx® $T_4$ assay.

Further, for the TDx®, TDxFLx™, and IMx® new $T_4$ assays, the minimum polarization span for the standard calibration curves is preferably at least 100 mP, more preferably greater than 125 mP or 130 mP. The commercially available assays have similar spans. The upper limit for the span is preferably less than 300 mP. To achieve the desired span, the tracer in the assays must bind to the antibody used and must effectively compete with endogenous $T_4$ present in a sample.

Additionally, by measuring the ratio of the concentrations of $T_4$ to triiodothyronine ($T_3$) which correspond to the midpoint of the polarization span for the $T_4$ standard curve, it was observed that the cross-reactivity of monoclonal antibody 1-189-252 with $T_3$ in the TDx® new $T_4$ assay was about 8%. Such low level of cross-reactivity is important because $T_3$ is another thyroid hormone in the human serum which resembles $T_4$. Therefore, for an accurate assay of $T_4$, it is important that the antibody against $T_4$ does not substantially cross-react with $T_3$. Thus, such cross-reactivity is preferably about 15% or less, and more preferably about 10% or less.

To compare the commercially available $T_4$ tracer and antibody to that of the present invention, a number of discrepant samples were run using the standard protocol of the commercially available Abbott TDx® $T_4$ assay, using: 1) the commercially available TDx® $T_4$ tracer and antibody; 2) the commercially available TDx® $T_4$ tracer, but monoclonal antibody 1-189-252 in place of the commercially available antibodies; 3) monoclonal antibody 1-189-252 and the tracer of Example 2, in place of the commercially available TDx® $T_4$ antibody and tracer. These samples were also run on Abbott Tetrabead-125® radioimmunoassay ($T_4$ RIA, Abbott Laboratories) according to the vendor's recommended protocol. Information regarding the TDx® assay method can be found in the TDx® System Operation Manuals. The TDx® System Operation Manuals contain: 1) theory of operation: fluorescerise polarization immunoassay; 2) operational precautions and limitations; 3) daily start-up procedure; 4) monthly and periodic procedures necessary for quality control to be maintained. The discrepant samples were obtained from patients whose samples gave a reading of zero or abnormally low level of thyroxine conccentration in the commercially available TDx® $T_4$ assay but a reading indicating the presence of or a higher level of thyroxine concentraion in a $T_4$ RIA assay.

The results of the above assays are as follows:

TABLE 1

| | $T_4$ (microgram/dL) | | | |
|---|---|---|---|---|
| DISCREPANT | 1. TDx® $T_4$ Assay Commercially Available Reagents | 2. TDx® $T_4$ Assay MAB 1-189-252 & *$T_4$ Tracer | 3. TDx® $T_4$ Assay MAB 1-189-252 & Tracer of Example 2 | 4. $T_4$ RIA |
| 1 | 1.97 | 0.0 | 9.80 | 10.26 |
| 2 | 0.0 | 0.0 | 6.78 | 7.02 |
| 3 | 2.21 | 0.0 | 6.17 | 6.41 |
| 4 | 1.04 | — | 7.97 | 9.39 |
| 5 | 0.0 | 0.0 | 7.03 | 8.23 |
| 6 | 0.0 | 0.0 | 5.34 | 4.63 |
| 7 | 0.0 | 0.0 | 12.75 | 15.95 |
| 8 | 0.0 | 0.0 | 8.82 | 10.16 |
| 9 | 2.65 | 2.24 | 7.03 | 8.18 |
| 10 | 0.0 | 0.0 | 15.85 | 15.43 |
| 11 | 3.31 | 0.89 | 7.78 | 8.71 |
| 12 | 2.37 | 0.0 | 8.57 | 10.05 |

In this table, "*$T_4$ tracer" denotes the commercially available $T_4$ tracer.

The above results demonstrate the effectiveness of the new tracer (column 3) yielding $T_4$ values within the expected range as compared to the $T_4$ RIA result.

The tracers and antibodies of the present invention can also be used in the IMx® and TDxFLx™ $T_4$ assays.

To determine whether the tracer was responsible for the falsely low $T_4$ reading in the discrepant samples, the following assays were conducted. The commercially available TDx® reagent pack contains three bottles of reagents, designated "S", "T", and "P" pots. The S pot contains the $T_4$ antibodies. The T pot contains the commercially available $T_4$ tracer $T_4$-FITC. The P pot contains the $T_4$ pretreatment solution which removes the protein from any protein bound thyroxine in order to release the thyroxine for assay. In the following, the commercially available assay was conducted with the exception that the S pot which normally contained the $T_4$ antibodies was replaced with a buffer solution. First, a discrepant serum sample (from one of the samples in Table 1) and a normal serum sample were tested and their results are shown in Table 2. As shown in Table 2, the assay gave a high mP value for the discrepant sample. In contrast, the normal sample generated a significantly lower mP value.

TABLE 2 mP VALUES IN THE PRESENCE OF COMMERCIALLY AVAILABLE $T_4$ TRACER AND ABSCENCE OF $T_4$ ANTIBODIES

| SAMPLE | mP Value |
|---|---|
| Discrepant | 206.13 |
| Normal Serum | 195.92 |

Then, the above described assay (wherein the S pot contained a buffer instead of antibodies) was conducted on the same discrepant samples as used in Table 1 and the results were shown in Table 3 below. One run was conducted with the commercially available tracer and one run was conducted with the tracer of Example 2. A reduction in mP was observed with the tracer of Example 2, demonstrating that the endogeneous immunoglobulins in the discrepant samples do not bind to the tracer of Example 2.

TABLE 3

Binding of Endogenous Immunoglobulins by Commercially Available Tracer and Tracer of Example 2

| | mP Value | |
|---|---|---|
| Discrepant | Commercially Available Tracer | Example 2 Tracer |
| 1 | 234.55 | 95.34 |
| 2 | 225.79 | 99.88 |
| 3 | 199.05 | 96.78 |
| 4 | 232.76 | 96.16 |
| 5 | 213.26 | 96.01 |
| 6 | 176.04 | 104.44 |
| 7 | 276.63 | 108.89 |
| 8 | 397.74 | 103.30 |
| 9 | 195.64 | 100.21 |
| 10 | 282.71 | 84.15 |
| 11 | 195.25 | 97.55 |
| 12 | 230.48 | 115.77 |

As described above, an evaluation of these discrepant serum samples demonstrated that the binding factor present was an immunoglobulin having an affinity for the commercially available $T_4$ tracer. The determination was accomplished by the following methods: HPLC, immunoblot analysis and protein G sepharose separation.

In the HPLC study, proteins found in discrepant patients were separated by HPLC using an anion exchange column. Fractions that had the ability to bind the $T_4$ tracer were isolated. These fractions corresponded to the region of the chromatographic profile where IgG would elute.

In addition, Immunoblot analysis of the selected fractions indicated a band corresponding to human IgG which was detected with goat α-human IgG.

These selected fractions were then incubated with Protein-G sepharose. Protein-G sepharose selectively binds IgG. Following removal of the Protein-G sepharose by centrifugation, an analysis of the supernatants revealed that the $T_4$ binding component was no longer present.

It would be clear to one skilled in the art that the assays utilizing the tracers and antibodies of the present invention can also be conducted on other FPIA instruments besides TDx®, TDxFLx™, and IMx®. The parameters, such as the span and concentration of thyroxine detectable, will be optimized according to the characteristics, such as the sensitvity, of each instrument used.

All publications and patent applications mentioned in this specification are herein incorporated by reference to the same extent as if each of them had been individually indicated to be incorporated by reference.

Although the foregoing invention has been described in some detail by way of illustration and examples for purposes of clarity and understanding, various modifications and changes which are within the skill of those skilled in the art are considered to fall within the scope of the appended claims. Future technological advancements which allow for obvious changes in the basic invention herein are also within the claims.

We claim:

1. A method of making an immunogen of the formula:

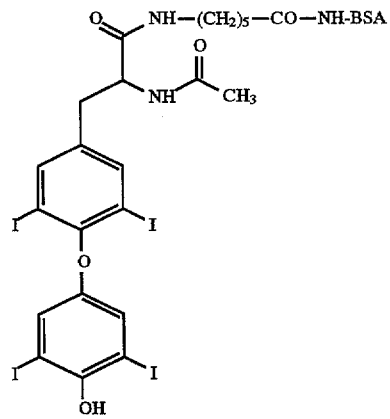

wherein BSA denotes bovine serum albumin, the degree of substitution of BSA by the thyroxine derivative is between 1% to 100%, the thyroxine is an L-isomer, and antibodies directed against the immunogen immunoreact with an L-thyroxine conjugate of the formula:

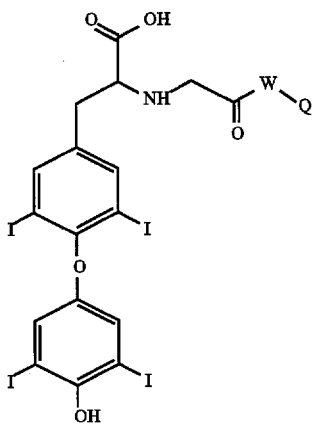

where Q is a detectable moiety and W is a linking moiety, the method comprising the steps of:

(a) N-acetylating L-thyroxine to form α-N-acetyl L-thyroxine;

(b) conjugating the αN-acetyl L-thyroxine to 6-aminocaproic acid to form a L-thyroxine conjugate; and (c) conjugating the L-thyroxine conjugate of step (b) to bovine serum albumin.

* * * * *

UNITED STATES PATENT AND TRADEMARK OFFICE
CERTIFICATE OF CORRECTION

PATENT NO. : 5,691,456
DATED : November 25, 1997
INVENTOR(S) : Adamczyk et al.

It is certified that error appears in the above-indentified patent and that said Letters Patent is hereby corrected as shown below:

Column 1, line 24, "tbyroxine" should be --thyroxine--;
      line 56, "monoclonai" should be --monoclonal--;

Column 11, line 27, "areinc" should be --amino--;
      line 42, "am" should be --are--.

Column 16, line 28, "Samples" should be --samples--.

Signed and Sealed this

Fifth Day of May, 1998

*Attest:*

BRUCE LEHMAN

*Attesting Officer*      *Commissioner of Patents and Trademarks*